US009360572B2

(12) United States Patent
Siedenburg

(10) Patent No.: US 9,360,572 B2
(45) Date of Patent: Jun. 7, 2016

(54) LIQUID MIXTURE USED TO TEST AND VALIDATE TEST DEVICES FOR INSPECTING OBJECTS OR PERSONS

(71) Applicant: Smiths Heimann GmbH, Wiesbaden (DE)

(72) Inventor: Uwe Siedenburg, Essenheim (DE)

(73) Assignee: Smiths Heimann GmbH, Wiesbaden (DE)

( * ) Notice: Subject to any disclaimer, the term of this patent is extended or adjusted under 35 U.S.C. 154(b) by 51 days.

(21) Appl. No.: 14/187,842

(22) Filed: Feb. 24, 2014

(65) Prior Publication Data

US 2015/0260858 A1    Sep. 17, 2015

Related U.S. Application Data

(63) Continuation of application No. PCT/EP2012/065948, filed on Aug. 15, 2012.

(30) Foreign Application Priority Data

Aug. 22, 2011    (DE) .......................... 10 2011 081 328

(51) Int. Cl.
| | |
|---|---|
| *G01T 7/00* | (2006.01) |
| *G01N 5/00* | (2006.01) |
| *G01N 23/06* | (2006.01) |
| *G01N 33/22* | (2006.01) |
| *G01V 5/00* | (2006.01) |
| *G01N 23/02* | (2006.01) |

(52) U.S. Cl.
CPC ................ *G01T 7/005* (2013.01); *G01N 23/02* (2013.01); *G01N 33/227* (2013.01); *G01V 5/0016* (2013.01)

(58) Field of Classification Search
CPC .............................. G01N 33/227; G01T 7/005
See application file for complete search history.

(56) References Cited

U.S. PATENT DOCUMENTS

| 2,498,277 A | 1/1950 | Navikas |
| 5,958,299 A | 9/1999 | Kury et al. |
| 6,839,406 B2 | 1/2005 | Ries et al. |
| 7,583,221 B2 | 9/2009 | Detlefsen et al. |

FOREIGN PATENT DOCUMENTS

| DE | 199 54 662 | 6/2001 |
| DE | 10 125 531 | 11/2002 |
| DE | 10 2005 016 106 | 10/2006 |
| DE | 10 2011 081 328 | 2/2013 |
| GB | 347144 | 10/1929 |
| WO | WO 2005/094768 A1 | 10/2005 |
| WO | WO 2009/136677 A1 | 11/2009 |

OTHER PUBLICATIONS

Sorby et al., "Dielectric Constants of Complex Pharmaceutical Solvent Systems I," J. of Pharma. Sci., vol. 52, No. 12, pp. 1149-1153 (Dec. 1, 1963).
Cox et al., "A Continuous-Flow, Rapid-Mixing, Photolabelling Technique Applied to the Acetylcholine Receptor," Analytical Biochemistry, vol. 136, No. 2, pp. 476-486 (Feb. 1, 1984).
Le Roux et al., "Preserving the Neurovascular Supply in the Hall-Findlay Superomedial Pedicle Breast Reduction: An Anatomical Study," J. of Plastic, Reconstructive & Aesthetic Surgery, vol. 63, pp. 655-662 (2010).
Herzen et al., "Quantitative Phase-Contrast Tomography of a Liquid Phantom Using a Conventional X-Ray Tube Source," Optics Express, Optical Soc. of Am., vol. 17, No. 12, pp. 10010-10018 (2009)

*Primary Examiner* — Jill Warden
*Assistant Examiner* — Julie Tavares
(74) *Attorney, Agent, or Firm* — Muncy, Geissler, Olds & Lowe, P.C.

(57) ABSTRACT

A liquid mixture is used to test and validate test devices for inspecting objects or persons, said mixture containing glycerol and sodium hydroxide, in a weight ratio of glycerol to solid hydroxide between 6.5 and 3.8, and containing water.

2 Claims, No Drawings

LIQUID MIXTURE USED TO TEST AND VALIDATE TEST DEVICES FOR INSPECTING OBJECTS OR PERSONS

This nonprovisional application is a continuation of International Application No. PCT/EP2012/065948, which was filed on Aug. 15, 2012, and which claims priority to German Patent Application No. 10 2011 081 328.4, which was filed in Germany on Aug. 22, 2011, and which are both herein incorporated by reference.

BACKGROUND OF THE INVENTION

1. Field of the Invention

Inspection systems, in which the persons or objects to be inspected are x-rayed or irradiated in screening devices by electromagnetic rays, are used for inspecting persons and objects, such as luggage, for hazardous materials, such as blasting materials or explosives. Such inspection systems are used at airports for inspecting passengers and luggage.

2. Description of the Background Art

The inspection systems according to a known embodiment contain screening devices in which the objects to be inspected, for example, luggage, are x-rayed or irradiated by x-rays and the transmitted or scattered x-rays are detected and analyzed (DE 10125531-A, DE 19954662-A).

Screening devices are known for inspecting persons, in which the persons to be inspected are irradiated with electromagnetic mm waves and the scattered mm waves are analyzed to obtain an image (DE 102005016106-A).

The screening devices must be tested and validated before being placed into operation. This typically occurs with real hazardous materials, therefore the explosives to be detected. The use of explosives is regulated by law, and moreover they are difficult to handle.

U.S. Pat. No. 5,958,299 discloses an explosive simulation mixture, which contains non-explosive components, whereby the components are selected so that the mixture has a physical form, density, x-ray transmission, and an effective atomic number that corresponds to a selected explosive mixture. An x-ray screening device can be tested for the detection of the specific explosive with the use of the simulation mixture instead of a real explosive. Solid, plastic, and gel-like compositions, which are made up of different components, are described as simulation mixtures.

Inspection systems are also increasingly required to detect liquid explosives and so-called "home-made explosives" as well.

SUMMARY OF THE INVENTION

It is therefore an object of the invention to provide a mixture that simulates blasting materials or explosives and is not explosive, non-critical in regard to handling, and economic to produce, and behaves like the real hazardous material in a screening device for inspecting objects or persons.

In an embodiment, the object is attained with a mixture of glycerol, sodium hydroxide (NaOH), and water, whereby glycerol and sodium hydroxide are present in a weight ratio of glycerol/sodium hydroxide between 6.5 and 3.8.

DETAILED DESCRIPTION

In a preferred simulation mixture, the amount of glycerol is 57% by weight to 78% by weight, particularly about 68% by weight, the amount of sodium hydroxide is 12% by weight to 15% by weight, particularly about 14% by weight, whereby the amount of water brings the amounts to 100% by weight, and is particularly about 18% by weight.

The invention thus provides the possibility of simulating explosive liquids as well. Simulation mixtures for various liquid hazardous materials can be prepared by different degrees of dilution with water.

The invention can be used preferably for testing and validating screening devices, capable of detecting liquid hazardous materials. To this end, the objects to be inspected, particularly luggage, are x-rayed or irradiated with electromagnetic rays. The transmitted or scattered rays are detected or captured and analyzed. The screening devices must be tested and validated to assure their functionality. During the validation it is checked whether the inspection system meets the predefined requirements.

For testing and validating, the liquid simulation mixture according to the invention is placed in an object to be inspected or on a person. The simulation mixture consists of glycerol, sodium hydroxide, and water.

A preferred use of a mixture according to the invention is the testing and validating of x-ray screening devices for inspecting persons or objects, particularly luggage, as they have been described as prior in the art in the introduction to the description.

A further preferred use of a mixture according to the invention is the testing and validating of screening devices that use electromagnetic mm waves for inspecting persons or objects, as they have been described as prior in the art also in the introduction to the description.

According to the basic formulation for the liquid simulation mixture, glycerol and sodium hydroxide (NaOH) are present in a weight ratio of glycerol/sodium between 6.5 and 3.8. Water is added to bring the mixture of glycerol and NaOH to 100% by weight. Preferably, the amount of glycerol is 57% by weight to 78% by weight, particularly about 68% by weight, and the amount of sodium hydroxide (NaOH) 12% by weight to 15% by weight, particularly about 14% by weight. The mixture of glycerol and sodium hydroxide (NaOH) is brought to 100% by weight with water, whereby the amount of water preferably is about 18% by weight.

The previously described basic formulation can be diluted or thickened with retention of the ratio between glycerol and sodium hydroxide by more or less water, whereby the total mixture remains liquid. Simulation mixtures for simulating various liquid hazardous materials can be produced by the different amounts of water.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A liquid mixture for testing and validating screening devices for inspecting objects or persons, the liquid mixture containing 68% by weight glycerol, 14% by weight sodium hydroxide and 18% by weight water,
   wherein the mixture is detectable as a simulative explosive material using x-ray or electromagnetic mm waves irradiated from a screening device.

2. A liquid mixture for testing and validating screening devices for inspecting objects or persons, the liquid mixture consisting of 68% by weight glycerol, 14% by weight sodium hydroxide and 18% by weight water, wherein the mixture is detectable as a simulative explosive material using x-ray or electromagnetic mm waves irradiated from a screening device.

\* \* \* \* \*